United States Patent [19]

Sounik et al.

[11] Patent Number: 5,463,108

[45] Date of Patent: Oct. 31, 1995

[54] PROCESS FOR PREPARING ACETOXYSTYRENE

[75] Inventors: James R. Sounik, Corpus Christi; William W. Wilkison, III, Richardson; Keith M. Russ; Lynn Massarelli, both of Corpus Christi, all of Tex.

[73] Assignee: Hoechst Celanese Corporation, Somerville, N.J.

[21] Appl. No.: 359,098

[22] Filed: Dec. 19, 1994

[51] Int. Cl.$^6$ .................................................. C07C 69/00
[52] U.S. Cl. ..................... 560/130; 560/142; 560/144; 560/231; 560/239; 568/337; 568/774
[58] Field of Search ........................................ 560/130, 138, 560/144, 239, 142, 231, 250, 251, 252, 254; 568/337, 774

[56] References Cited

U.S. PATENT DOCUMENTS

| | | | |
|---|---|---|---|
| 4,032,513 | 6/1977 | Fujiwara et al. | 526/141 |
| 4,927,956 | 5/1990 | Vicari et al. | 560/130 |
| 4,965,400 | 10/1990 | Vicari et al. | 560/130 |
| 5,041,614 | 8/1991 | Aslam et al. | 560/130 |
| 5,072,025 | 12/1991 | Vicari et al. | 560/130 |
| 5,084,533 | 1/1992 | Shah et al. | 526/75 |
| 5,087,772 | 2/1992 | Sheehan et al. | 568/804 |
| 5,151,546 | 9/1992 | Shah et al. | 560/130 |
| 5,245,074 | 9/1993 | Shah et al. | 560/130 |
| 5,247,124 | 9/1993 | Aslam et al. | 560/130 |
| 5,274,175 | 12/1993 | Shah et al. | 560/130 |

*Primary Examiner*—Arthur C. Prescott
*Attorney, Agent, or Firm*—James J. Mullen; Donald R. Cassady

[57] ABSTRACT

The present invention provides a unique and novel way of producing 4-acetoxystyrene. In this new process, 4-hydroxystyrene is acetylated, in the presence of an acetylation agent, under suitable conditions of temperature and pressure and for a sufficient period of time to form acetoxystyrene.

14 Claims, No Drawings

PROCESS FOR PREPARING ACETOXYSTYRENE

BACKGROUND OF THE INVENTION

1. Field of the Invention

The present invention relates to a method for the preparation of 4-acetoxystyrene (ASM), and more particularly, for the preparation of 4-acetoxystyrene from 4-hydroxystyrene (HSM).

2. Description of the Prior Art

4-Acetoxystyrene (ASM) is a well-known compound which is useful as an intermediate in the preparation of compounds useful in the production of adhesives, photoresists, etc. The preparation of 4-acetoxystyrene is well-known in the art, however, a more efficient process for preparing 4-acetoxystyrene is desired and needed. The instant invention provides a method whereby increased yields are obtained.

The following prior art references are disclosed in accordance with the terms of 37 CFR 1.56, 1.97 and 1.93.

U.S. Pat. NO. 5,087,772 (issued Feb. 11, 1992) discloses the preparation of HSM by reacting 4-acetoxystyrene (ASM) with a suitable alcohol in the presence of a catalytic amount of a suitable base.

European Patent Application 0-128-984 (publication number) filed Aug. 30, 1983 discloses a process for the production of para-vinyl phenol (HSM) by dehydrogenation of paraethyl phenol.

European Patent Application 01-08-624 (publication number) filed Nov. 4, 1983 discloses a process for the production of p-vinyl phenol polymer (polyhydroxystyrene polymer—PHS) by polymerizing p-vinylphenol (HSM) in the presence of water and iron.

U.S. Pat. No. 4,032,513 (issued Jun. 28, 1977) discloses a process of producing PHS by cationically polymerizing HSM in the presence of a nitrile, such as $CH_3CN$, using a cationic polymerization initiator in a homogeneous reaction system.

U.S. Pat. No. 5,041,614 discloses a method for the preparation of 4-acetoxystyrene (ASM) from 4-acetoxyphenylmethylcarbinol. (Note Formula I for the structural formula for ASM).

U.S. Pat. No. 5,084,533 discloses a process for the neat hydrogenation of4-acetoxyacetophenone in the production of 4-acetoxystyrene (ASM).

U.S. Pat. No. 5,151,546 discloses a process for preparing 4-acetoxystyrene (ASM) by heating 4-acetoxyphenylmethylcarbinol with an acid catalyst.

U.S. Pat. No. 5,245,074 discloses a process for preparing 4-acetoxystyrene (ASM) through the 4-acetoxyacetophenone/4-acetoxyphenylmethylcarbinol route.

U.S. Pat. No. 5,247,124 discloses a process for preparing substituted styrenes such as ASM by reacting a bisarylalkyl ether in the presence of an acid catalyst.

All of the above cited prior art and any other references mentioned herein are incorporated herein by reference in their entirety.

3. Additional Background Information

This patent application is assigned to the same assignee of that pending patent application Ser. No. 08/029,200 filed Mar. 10, 1993 and entitled "Process for the Preparation of P-α-aminoethylphenol" (PEP) and which is incorporated herein by reference in its entirety ("α" means alpha herein).

SUMMARY OF THE INVENTION

The present invention provides a unique and novel way of producing 4-acetoxystyrene (monomer) (ASM). In this new process, 4-hydroxystyrene (HSM) is acetylated, in the presence of an acetylating agent, under suitable conditions of temperature and pressure and for a sufficient period of time to form the 4-acetoxystyrene (ASM).

DETAILED DESCRIPTION OF THE INVENTION

It has unexpectedly been found that HSM can be prepared by acetylating HSM, in the presence of an acetylating agent with or without a diluent or solvent and/or catalyst, for a sufficient period of time under suitable conditions.

The process of the present invention is carried out at a reaction temperature of at least 20° C., preferably between 30° C. and 200° C., and more preferably between 50° C. and 150° C. The reaction pressure may be subatmospheric, atmospheric or superatmospheric. Atmospheric pressure is generally preferred.

The length of time which this acetylation step is conducted is not critical and the only requirement is that the acetylation be conducted for a period sufficient to form ASM. Generally, this period is at least five minutes and may be as long as five hours.

The acetylation agent is acetic anhydride, acetic acid, acetyl chloride, or mixtures thereof. The amount of such agent used is not critical; however, it is necessary that the molar ratio of acetylation agent to HSM be at lest about 1: 1, preferably from about 1: 1 to about 5: 1.

When the acetylation agent is acetic acid, one may employ a catalyst to facilitate the reaction. Any catalyst can be used as long as the desired end result is achieved. Preferably acid catalysts are used. These acid catalysts include, without limitation, phosphoric acid, p-toluene-sulfonic acid, methane-sulfonic acid, ammonium bisulfate, potassium bisulfate, $H_2SO_4$ and HCl. The amount of catalyst required varies from catalyst to catalyst. In all instances, however, the amount is very small compared to the amount of reactant. In the present case, the amount of catalyst employed is usually less than one mole of catalyst per 100 moles of reactant, e.g. HSM.

Diluents/Solvents which can be used in the present invention include: (a) hydrocarbons such as benzene, toluene, xylene, and low-boiling point petroleum fractions; (b) inorganic gases such as carbon monoxide, carbon dioxide, nitrogen, helium, and argon; (c) dipolar aprotic solvents; and (d) mixtures thereof. The dipolaf aprotic solvents employed are solvents which have a high dielectric constant and a high dipole moment but no acid hydrogen atoms; for example, such solvents include dimethylsulfoxide (DMSO), acetonitrile, dimethylformamide (DMF), dimethylacetamide, hexamethylphosphoric acid triamide (HMPT), and n-methylpyrrolidone (NMP). Benzene and toluene are preferred diluents. The diluents are used in an amount of 2 to 200 moles, preferably 3 to 20 moles per mole of HSM. It is to be understood that any diluent may be used under any temperature and reaction conditions so long as the acetylation of HSM is effected smoothly.

After the acetylation of HSM, the end product ASM is recovered from the reaction product and the residual fraction containing any unreacted HSM can be recycled as the starting material for the next cycle of acetylation. The end product ASM may be recovered from the reaction product by any method. One example is to recover the ASM as a polymerized product, i.e., the reaction product is first subjected to a polymerization step to polymerize the ASM and the resulting polymer is separated from the fraction containing the unreacted HSM by distillation or any other suitable technique.

In another facet of the present invention, the HSM starting material can be prepared from p-α-aminoethylphenol, sometimes referred to as p-vinylphenol, which is designated AEP herein.

4-Hydroxystyrene (HSM) is a well-known compound which is itself useful as a food flavoring substance and as an intermediate in the preparation of polymers and copolymers useful in coatings, electronic applications, ion exchange resins, photoresists, etc.

Although there are several known ways to prepare 4-hydroxystyrene, those known methods are not commercially feasible in the further utilization of the 4-hydroxystyrene. The 4-hydroxystyrene itself is difficult to isolate, since if (1) readily decomposes, (2) is toxic via skin absorption, and (3) readily polymerizes and as a result, those skilled in the art have made numerous attempts to find a method of synthesizing 4-hydroxystyrene in a manner which avoids polymerization and provides the 4-hydroxystyrene in a medium which can be utilized to prepare particular derivatives therefrom.

A preparation for 4-hydroxystyrene utilizing 4-acetoxystyrene (ASM) is reported in a paper entitled, "Preparation of Vinyl-Phenols & Isopropylphenols", Corson et al., Volume 23, April 1958, J. Org. Chem. In this preparation, 4-acetoxystyrene is saponified in an aqueous system with a large concentration of a base, KOH, to produce an aqueous solution of the potassium salt of 4-hydroxystyrene which is neutralized with acid to precipitate 4-hydroxystyrene. As indicated above, the procedure is not practical or commercially feasible for production of large quantities of 4-hydroxystyrene because the 4-acetoxystyrene and/or the 4-hydroxystyrene is not very stable and readily polymerizes under the aqueous saponification conditions employed herein, which involve high concentrations of soluble base, resulting in poor yields of 4-hydroxystyrene. Thus, a more efficient process for producing 4-hydroxystyrene is desired and needed.

In another part of the present invention, there is provided a unique and novel way of producing vinyl phenols such as p-vinylphenol (4-hydroxystyrene - HSM). In this new process, p-α-aminoethylphenol (AEP) is heated, with or without a diluent or solvent, under suitable deamination conditions of temperature and pressure and for a sufficient period of time to form the hydroxystyrene (HSM).

The AEP to HSM process of the present invention is carried out at a reaction temperature of at least 50° C., preferably between 80° C. and 200° C., and more preferably between 80° C. and 100° C. The reaction pressure may be subatmospheric, atmospheric, or superatmospheric. Atmospheric pressure is generally preferred.

The length of time which this heating step is conducted is not critical and the only requirement is that the heating be conducted for a period sufficient to form HSM Generally, this period is at least five minutes and may be as long as five hours.

Diluents/solvents which can be used in this facet of the present invention include: (a) water; (b) hydrocarbons such as benzene, toluene, xylene, and low-boiling point petroleum fractions; (c) inorganic gases such as carbon monoxide, carbon dioxide, nitrogen, helium, and argon; (d) dipolar aprotic solvents; and (e) mixtures thereof. The dipolar aprotic solvents employed are solvents which have a high dielectric constant and a high dipole moment but no acid hydrogen atoms; for example, such solvents include dimethylsulfoxide (DMSO), acetonitrile, dimethylformamide (DMF), dimethylacetamide hexamethylphosphoric acid triamide (HMPT), and n-methylpyrrolidone (NMP). Water, benzene, and toluene are preferred diluents. The diluents are used in an amount of 2 to 200 moles, and preferably 3 to 20 moles per mole of AEP. It is to be understood that any diluent may be used under any temperature and reaction conditions so long as the deamination of AEP is effected smoothly.

After the deamination of AEP, the end product (HSM) is recovered from the reaction product, and the residual fraction containing any unreacted AEP can be recycled as the starting material for the next cycle of deamination. The end product (HSM) may be recovered from the reaction product by any method, and thus, it is used as the starting material to o prepare ASM as described above.

The following specific example is supplied for the purpose of better illustrating the invention. This example is not intended, however, to limit or restrict the scope of the invention in any way and should not be construed as providing conditions, parameters, or values which must be utilized exclusively in order to practice the present invention.

EXAMPLE 1

Into a one liter flask equipped with a reflux condenser was charged a mixture of AEP (11.89 grams/0.087 moles) and toluene (50 milliliters). External heating was supplied and the resultant mixture was refluxed (at about 115° C.) for about 45 minutes. During this time, substantial quantities of ammonia were given off. GC analysis showed the presence of HSM.

EXAMPLE 2

Into the one liter flask and its HSM contents (from Example 1), there was added 17.87 grams (0.2 moles) of acetic anhydride. The resultant mixture was stirred and then heated and refluxed for two hours. The mixture was cooled to room temperature (about 20° C.) and the solvents removed by rotovaping The product was a clear amber oil and weighed 11.45 grams. GC - MS analyses showed the product to be 4-acetoxystyrene.

While the above has been described using p-a-aminoethylphenol (AEP) as the starting material, it is also within the scope of the present invention to use (1) other aminoethylphenols (wherein the aminoethyl and the hydroxy substituents are positioned at different locations on the phenyl ring), and (2) substituted aminoethylphenols wherein the remaining four hydrogen atoms are selectively replaced by an R group, said R being selected from the group consisting of (a) $C_1$–$C_8$ alkyl; (b) $C_6H_5$; (c) halogen (F, Cl, Br, I); (d) hydroxy; and (e) OR where R is the same as defined above. These aminoethylphenols and substituted aminoethylphenols are all suitable starting materials for use in the present invention processes.

Although the invention has been illustrated by the preceding example, it is not to be construed as being limited thereby; but rather, the invention encompasses the generic area as hereinbefore disclosed. Various modifications and embodiments can be made without departing from the spirit and scope thereof.

What is claimed is:

1. A process for preparing acetoxystyrene which comprises the step of acetylating 4-hydroxystyrene in the presence of an acetylating agent under suitable conditions of temperature and pressure and for a sufficient period of time to form said acetoxystyrene.

2. The process as set forth in claim 1 wherein the temperature is at least about 20° C.

3. The process as set forth in claim 1 wherein the reaction takes place in the presence of an aprotic organic solvent.

4. The process as set forth in claim 1 wherein the acetylation agent is selected from the group consisting of acetic anhydride, acetic acid, and acetyl chloride.

5. The process as set forth in claim 1 wherein the acetylation agent is acetic acid and there is also present an acetylation catalyst.

6. The process as set forth in claim 1 wherein the temperature is from about 50° C. to about 140° C.

7. A process for preparing acetoxystyrene which comprises the steps of (1) heating p-α-aminoethylphenol under suitable deamination conditions of temperature and pressure for a sufficient period of time to form 4-hydroxystyrene; and (2) acetylating said 4-hydroxystyrene in the presence of an acetylating agent under suitable conditions of temperature and pressure and for a sufficient period of time to form said acetoxystyrene.

8. The process as set forth in claim 7 wherein in step (1), the temperature is at least about 50° C.

9. The process as set forth in claim 7 wherein in step (1), there is also present a diluent.

10. The process as set forth in claim 7 wherein in step (1), the reaction takes place in the presence of an organic solvent.

11. The process as set forth in claim 7 wherein in step (1), the reaction takes place in the presence of water.

12. The process as set forth in claim 7 wherein in step (1), the temperature is from about 80° C. to about 100° C.

13. The process as set forth in claim 7 wherein, in step (1), an aminoethylphenol is substituted for p-α-aminoethylphenol.

14. The process as set forth in claim 7 wherein, in step (1), a substituted aminoethylphenol is substituted for p-α-aminoethylphenol.

* * * * *